United States Patent
Zvuloni

(10) Patent No.: US 7,407,501 B2
(45) Date of Patent: Aug. 5, 2008

(54) APPARATUS AND METHOD FOR COMPRESSING A GAS, AND CRYOSURGERY SYSTEM AND METHOD UTILIZING SAME

(75) Inventor: Roni Zvuloni, Haifa (IL)

(73) Assignee: Galil Medical Ltd., Yokneam (IL)

( * ) Notice: Subject to any disclaimer, the term of this patent is extended or adjusted under 35 U.S.C. 154(b) by 669 days.

(21) Appl. No.: 11/055,597

(22) Filed: Feb. 11, 2005

(65) Prior Publication Data

US 2005/0224085 A1    Oct. 13, 2005

Related U.S. Application Data

(63) Continuation of application No. 09/987,689, filed on Nov. 15, 2001, now abandoned, which is a continuation-in-part of application No. 09/860,486, filed on May 21, 2001, now Pat. No. 6,706,037.

(60) Provisional application No. 60/242,455, filed on Oct. 24, 2000.

(51) Int. Cl.
*A61B 18/02* (2006.01)
(52) U.S. Cl. ......................... 606/20; 128/898
(58) Field of Classification Search .............. 606/20–26; 128/898
See application file for complete search history.

(56) References Cited

U.S. PATENT DOCUMENTS

| | | | |
|---|---|---|---|
| 636,013 A | 10/1899 | Tolle | |
| 862,867 A | 6/1907 | Eggleston | |
| 2,700,876 A | 1/1955 | Gagnan | |
| 3,524,714 A | 8/1970 | Grove et al. | |
| 3,664,344 A | 5/1972 | Bryne | |
| 3,864,060 A | 2/1975 | Hall et al. | |
| 3,963,377 A | 6/1976 | Elliott et al. | |
| 4,515,516 A | 5/1985 | Perrine et al. | |
| 4,673,415 A | 6/1987 | Stanford | |
| 4,750,869 A | 6/1988 | Shipman, III | |
| 5,133,360 A | 7/1992 | Spears | |
| 5,224,930 A | 7/1993 | Spaeth et al. | |
| 5,647,868 A | 7/1997 | Chinn | |
| 5,716,353 A | 2/1998 | Matsuura et al. | |
| 5,746,736 A | 5/1998 | Tankovich et al. | |
| 5,800,484 A | 9/1998 | Gough et al. | |
| 5,800,487 A | 9/1998 | Mikus et al. | |
| 5,807,083 A | 9/1998 | Tomoiu | |
| 5,899,897 A | 5/1999 | Rabin et al. | |
| 5,902,299 A | 5/1999 | Jayaraman | |
| 5,916,212 A | 6/1999 | Baust et al. | |

(Continued)

FOREIGN PATENT DOCUMENTS

EP    0608927    3/1994

(Continued)

*Primary Examiner*—Michael Peffley
*Assistant Examiner*—Pete J Vrettakos

(57) ABSTRACT

An apparatus for compressing a gas and its uses are disclosed. The apparatus comprises a fixed-volume container having a hollow and a moveable element subdividing said hollow into a first variable-volume portion and a second variable-volume portion, the second variable-volume portion having an opening for introducing therein a hydraulic and/or pneumatic fluid under pressure, for causing an increase in the volume of said second variable-portion by moving said moveable element, thereby, consequently, decreasing the volume of the first variable-volume portion and compressing a gas contained therein.

14 Claims, 8 Drawing Sheets

U.S. PATENT DOCUMENTS

| | | |
|---|---|---|
| 5,964,796 A | 10/1999 | Imran |
| 5,978,697 A | 11/1999 | Maytal et al. |
| 5,993,172 A | 11/1999 | Schuman et al. |
| 5,993,444 A | 11/1999 | Ammar et al. |
| 5,993,471 A | 11/1999 | Riza et al. |
| 6,009,877 A | 1/2000 | Edwards |
| 6,039,730 A | 3/2000 | Rabin et al. |
| 6,053,937 A | 4/2000 | Edwards et al. |
| 6,106,518 A | 8/2000 | Wittenberger et al. |
| 6,129,670 A | 10/2000 | Burdette et al. |
| 6,139,544 A | 10/2000 | Mikus et al. |
| 6,142,991 A | 11/2000 | Schatzberger |
| 6,152,894 A | 11/2000 | Kubler |
| 6,179,831 B1 | 1/2001 | Bliweis |
| 6,190,378 B1 | 2/2001 | Jarvinen |
| 6,206,832 B1 | 3/2001 | Downey et al. |
| 6,231,570 B1 | 5/2001 | Tu et al. |
| 6,264,679 B1 | 7/2001 | Keller et al. |
| 6,270,494 B1 | 8/2001 | Kovalcheck et al. |
| 6,287,326 B1 | 9/2001 | Pecor |
| 6,306,129 B1 | 10/2001 | Little et al. |
| 6,330,478 B1 | 12/2001 | Lee et al. |
| 6,383,144 B1 | 5/2002 | Mooney et al. |
| 6,383,181 B1 | 5/2002 | Johnston et al. |
| 6,419,462 B1 | 7/2002 | Horie et al. |
| 6,468,268 B1 | 10/2002 | Assoud et al. |
| 6,505,629 B1 | 1/2003 | Mikus et al. |
| 6,613,044 B2 | 9/2003 | Carl |
| 6,706,037 B2 | 3/2004 | Zvuloni et al. |
| 2002/0188287 A1 | 12/2002 | Zvuloni et al. |
| 2003/0181896 A1 | 9/2003 | Zvuloni et al. |
| 2004/0049177 A1 | 3/2004 | Zvuloni et al. |

FOREIGN PATENT DOCUMENTS

| | | |
|---|---|---|
| EP | 0624347 | 11/1994 |
| EP | 0651308 | 3/1995 |
| EP | 0947172 | 6/1999 |
| EP | 1048272 | 2/2000 |
| WO | WO 96/37158 | 11/1996 |
| WO | WO 02/34106 | 2/2002 |

APPARATUS AND METHOD FOR COMPRESSING A GAS, AND CRYOSURGERY SYSTEM AND METHOD UTILIZING SAME

This is a continuation of U.S. patent application Ser. No. 09/987,689, filed Nov. 15, 2001 which is abandoned, which is a continuation-in-part of U.S. patent application Ser. No. 09/860,486, filed May 21, 2001, now U.S. Pat. No. 6,706,037, which claims the benefit of priority from U.S. Provisional Patent Application No. 60/242,455, filed Oct. 24, 2000, now expired.

FIELD AND BACKGROUND OF THE INVENTION

The present invention relates to apparatus and method for compressing and/or re-compressing gas and further to the use of in situ gas compression as a source of compressed gas to a compressed gas utilizing application, such as a cryoablation apparatus.

Many methods are known in the art for mechanically compressing (pressurizing) gas, for storing compressed (pressurized) gas in containers, for transporting compressed gas to sites where the compressed gas is to be used, and for utilizing compressed gasses for a variety of purposes in a variety of utility applications.

Gas compression is most typically accomplished using single stage or multiple stage reciprocating piston systems powered by independent power sources such as electric motors or internal combustion engines.

Alternatively, low and medium pressure gasses are sometimes raised to a higher pressure via the use of what is known in the art as "booster" pumps. One popular form of a booster pump does not require external power sources. In these pumps the pressure of the input gas itself is applied over the surface of a large area piston which, by mechanical linkage, induces movement in a small area piston. The small area piston is used to compress a portion of the input gas to a higher level of compression.

In many usages of compressed gas, heavy-duty equipment for pressurizing gas is located at a gas supply facility distant from the utilization site itself. Pressurized gas is typically transported to the utilization site in pressurized gas containers such as gas cylinders. At the utilization site, the gas containers are coupled to the application that utilizes the compressed gas. During utilization, the gas containers are gradually emptied until the residual pressure of the gas in the containers becomes too low for the particular application. The containers are then typically uncoupled from the application and returned to the gas supply facility, where they are refilled and re-pressurized.

For many industrial, domestic, recreational, and other uses, these prior art methods are adequate. With respect to some applications, however, limitations and disadvantages of these prior art methods are apparent.

Reciprocating piston compression systems typically require lubrication, and volatilization of the lubricants can compromise the purity of the compressed gas.

Thus there is a widely recognized need for, and it would be highly advantageous to have, a method and apparatus for gas compression not involving the large rapid and continuous mechanical movements typical of reciprocating piston systems, and not requiring lubrication of the moving parts.

The phrases "medium pressure" and "medium pressure gas" are used herein to refer to gasses in a range of pressures customarily used in industrial processes, and customarily supplied by industrial supply sources. Compressed argon, used for a variety of industrial purposes, is typically supplied at a pressure of about 2500 PSI. For argon, pressures in this range are referred to herein as "medium" pressures.

The phrases "high pressure" and "high pressure gas" are used herein to refer to gasses in a range of pressures above medium pressure. Various compressed gas utilizing applications require the use of high pressure gas. Compressed argon for use in cryosurgery applications, for example, is typically required to be in the range of 3000-4500 PSI and above.

The prior art methods of supplying high pressure gas to high pressure gas applications are problematic in several respects.

One practical problem encountered in using high pressure gas in applications is that some high pressure gasses are simply not commercially available in many regions of the world. This problem exists even in some highly industrialized regions. In Japan, for example, argon gas, which is used in welding and other industrial processes, is available in popular industrial medium-pressure concentrations, yet high pressure argon gas is not commercially available in Japan. A Japanese utilization site, such as a cryosurgery site, requiring high pressure argon gas, must import this gas from outside the country.

A second practical problem in the use of prior art methods for supplying high pressure gas to a high pressure gas application is that transporting high pressurize gas can be inconvenient and/or dangerous. High pressure gas requires containers that are stronger and heavier than containers used for housing moderate pressurize gas. Transportation is more problematic as well. It may be considered more dangerous to transport high pressurize gas by air transportation, for example.

Thus, there is a widely recognized need for, and it would be highly advantageous to have, a method and apparatus for supplying high pressurize gas to a high pressurize gas application, using gas from popularly available medium pressure sources. Such an apparatus and method would overcome the practical difficulties of acquiring high pressure gas and the practical difficulties of transporting high pressurize gas.

A third problem in the use of prior art methods for supplying gas to high pressure gas applications is that a significant portion of gas so supplied cannot be used for its intended purpose. When gas is supplied in pressurized containers connected directly to the utilization mechanisms, the pressure of the gas in the supplied container gradually falls as the gas is used. Gas pressure in the container eventually drops to a point where it is lower than the minimum pressure required for the high-pressure application. At this point, considerable gas still remains in the container. This situation has the practical disadvantage that the container must then be returned to the gas supplier for refilling while still containing a significant quantity of unused gas, which is inconvenient. It also has the commercial disadvantage that in many cases suppliers do not credit their customers for the returned gas, so that the customer often pays for gas which was supplied to him but which he could not use.

There is, thus, also a widely recognized need for, and it would be highly advantageous to have, a method and apparatus for utilizing compressed gas which enables full use of all, or at least substantially most, of the gas supplied in a gas supply container.

There are, of course, some compressed gas utilizing applications in which re-pressurization and re-use of gasses is impractical. In some uses of compressed gas the cost of pressurizing and transporting the gas is relatively greater than the cost of manufacturing or isolating the gas. Pressurized air provides an example. For such gasses there would be little point in recycling the gas after use. In other cases, a pressurized gas is chemically transformed during utilization. Flammable gasses used for combustion are an example. Here too, recycling the gas is not generally practical.

In some applications, however, recycling is possible and in many cases eminently desirable. This is the case, for example, in compressed gas utilizing applications utilizing a gas which is rare, or is expensive to produce or to isolate, and in which the gas is not chemically transformed when utilized. A cryosurgery system utilizing krypton gas is an example of such an application.

Cryosurgery systems based on Joule-Thomson heat exchangers (also commonly referred to as Joule-Thomson devices) use compressed gas for heating and intense cooling of therapeutic cryoprobes used to ablate tissues within the body. The design of such applications is based on the fact that a compressed gas changes temperature as it moves from a region of high pressure to a region of low pressure. The gasses used do not enter into chemical interactions with their environment, they simply expand and contract, liquefy and evaporate.

Krypton presents advantages over the more popular argon gas for this application. For reasons connected with the physical characteristics of the gas, a krypton-based cryosurgery system can function at a lower pressure than an argon-based system, consequently is easier to build, maintain, and use. Yet krypton is considerably more expensive than argon, on the order of one hundred times more expensive in today's market. In a prior art system, where the compressed gas used in cryosurgery is, after decompression through use, simply vented to the atmosphere, use of the otherwise desirable krypton gas would be wasteful and expensive.

Thus, there is a widely recognized need for, and it would be highly advantageous to have, system and method for re-pressurizing and reusing gasses utilized in compressed gas utilizing applications, cryosurgery applications in particular.

The limitations and disadvantages of the prior art in the field of gas compression and the use of compressed gasses are particularly clear in the context of cryosurgery. Various medical conditions require the ablation of unhealthy tissues within the body. Techniques for cryoablation developed in recent years present various advantages over other ablation techniques, in particular the advantage of causing less damage to healthy tissues in proximity to the tissues whose removal or destruction is desired. Invasive surgical procedures require cutting or destroying tissues between the exterior of the body and the particular site whose destruction is desired. Less invasive procedures have been used, which bring about the destruction of selected tissues using probes which penetrate to the area to be operated and destroy the selected tissue by transferring energy to those tissues. RF energy, light (laser) energy, microwave energy, and high-frequency ultra-sound energy have been used in this context. However all such methods have the common disadvantage that while they raise the temperature of the tissues whose destruction is intended, they transfer heat to healthy tissues as well, causing their destruction, partial destruction, or functional impairment. Moreover, in some cases tissues exposed to thermal energy or other forms of energy that raise their temperatures secrete substances toxic to adjacent healthy tissues. For these and other reasons, cryoablation has become a popular method for certain types of ablation procedures. Examples are the treatment of prostate tumors and of benign prostate hyperplasia (BPH), and the creation of trans-myocardial channels to effect trans-myocardial revascularization.

According to a popular cryosurgical methodology, highly compressed gas is employed to cool and to heat surgical probes used for cryoablation of tissues. A preferred technology for effecting cryoablation involves the use of Joule-Thomson heat exchangers (also popularly known as "Joule-Thomson devices") for cooling and for heating of cryoprobes at the site of tissues to be cryoablated. U.S. Pat. No. 6,142,991 to Schatzberger and U.S. Pat. No. 5,978,697 to Maytal, et al, provide examples of systems using such devices.

To cool a cryosurgical apparatus utilizing a Joule-Thomson heat exchanger, a gas such as argon, nitrogen, air, krypton, $CF_4$, xenon, $N_2O$, or a mixture of similar gasses, under high pressure, is allowed to pass through an orifice into a chamber where the gas can expand. Expansion of the gas causes it to cool and may cause it to liquefy, or further liquefy. This process cools the chamber. Gasses which cool such a chamber after passing through such an orifice from an area of high pressure to an area of lower pressure are referred to herein as "cooling gasses." If the chamber is constructed of thermally conductive material such as a metal, cooling the chamber cools materials in proximity to the chamber as well. Cryoprobes for cryoablation are typically designed and constructed according to this principle. Cryoprobes using expansion of a high-pressure cooling gas through a Joule-Thomson orifice into a chamber constructed of thermally conductive material are used to cool body tissues in close proximity to the cryoprobe, to effect cryoablation.

Cryosurgical procedures sometimes also require heating of cryoprobes. Tissues undergoing cryoablation tend to adhere to the cold cryoprobe. Heating the cryoprobe subsequent to cryoablation causes melting at areas of contact between the cryoprobe and the tissues, thereby eliminating adherence of the tissues to the cryoprobe and allowing the cryoprobe to be easily removed from the cryoablation site. Cryoprobes may be heated, as well as cooled, using a Joule-Thomson heat exchanger. High-pressure helium or a similar gas passing through a Joule-Thomson orifice and expanding in a chamber, heats the chamber. Gasses which heat such a chamber after passing through such an orifice from an area of high pressure to an area of lower pressure are referred to herein as "heating gasses." If the chamber is constructed of thermally conductive material such as a metal, heating the chamber has the effect of heating materials in proximity to the chamber. This effect is used in the construction and utilization of cryoprobes to melt material adjacent to a cryoprobe subsequent to cryoablation, thereby enabling disengagement of the cryoprobe from the operated tissues.

Cryosurgical equipment using Joule-Thomson heat exchangers and utilizing popular and easily available cooling gasses, such as argon, require for their efficient operation a source of high pressure cooling gas, typically in the pressure range of 3000 PSI to 4500 PSI.

The need for high pressure gasses for efficient operation of cryosurgical equipment raises the several practical problems discussed hereinabove. Argon, for example, is a preferred gas for cooling in cryosurgical equipment based on Joule-Thomson devices. High pressure argon is more expensive than argon at standard industrial pressures, and in some locations, such as Japan, high pressure argon is not available at all. Argon can of course be purchased from standard industrial supply sources, but only at the medium pressures customarily used in industrial processes, typically around 2500 PSI. The pressure of easily commercially available industrial compressed argon is lower than the pressures required for efficient cooling of cryosurgical equipment using argon in a Joule-Thomson heat exchanger.

Thus, there is a widely recognized need for, and it would be highly advantageous to have, a method and apparatus for cryoablation wherein containers of gas pressurized to moderate pressure, such as are available from standard industrial sources of supply, are used to supply gas to a cryosurgury apparatus requiring gas of high pressure to effect cryogenic cooling.

An additional problem connected with the high-pressure requirements of cryosurgery is that even in regions of the world where high-pressure cooling and heating gasses are commercially available, their utilization is awkward and expensive. Gasses supplied in a high-pressure container can be utilized only until the pressure of gas in the container falls to the minimum pressure usable in cryosurgery. According to the methods of prior art, once pressure in a gas supply container falls below the minimum pressure required for cryosurgery, the gas supply container can no longer be utilized as a cryosurgery gas source, despite the fact that a considerable amount of cooling (or heating) gas may yet remain in the tank. If for example a cryoprobe requires a pressure of 4500 PSI (a typical figure) and a full container of gas is initially pressured to 6000 PSI, then only 25% of the supplied gas can be used for cryosurgery. As soon as more than one fourth of the gas initially contained in the container has been used, pressure in the container falls below the 4500 PSI minimum required by such a cryoprobe. In the case of a cryoprobe operating at 3250 PSI the situation is only slightly better: only approximately 46% of the gas contained in a 6000 PSI container can be used before pressure in the container falls below the minimum pressure required for operation of the cryoprobe.

Once pressure in a gas supply container falls below the minimum required for operation of a cryoprobe, the container must be returned to a gas supplier re-filling. In practice, some suppliers credit users for the unused gas returned to them in such a container. Other suppliers do not. In either case, the expense and bother occasioned by the necessity of switching containers, and the necessity of returning containers to a supplier for refilling while they yet contain substantial amounts of useful gas, are significant disadvantages of cryosurgical equipment and procedures, according to the known methods of prior art.

Thus, it would be desirable and advantageous to have a method and system for utilization of compressed gas in cryosurgery, and in similar applications, permitting utilization of substantially all or most of the contents of each container of supplied gas.

Prior art cryosurgery systems also suffer from the disadvantage that they do not re-use pressurized gas. The advantages (lower pressure requirements) of krypton gas over argon gas for use in cryosurgery systems are well known. Yet, it is largely impractical to use Krypton gas in prior art cryogenic systems, wherein the cooling gas is used for cryogenic cooling only once, and then is allowed to escape to the atmosphere.

Thus, there is a widely recognized need for, and it would be highly advantageous to have, an apparatus and method for re-pressurizing and re-utilizing the pressurized gasses in some compressed gas systems, particularly systems which utilize gasses that are rare or expensive to produce or isolate, and in which the gasses are not chemically altered when used. In cryosurgery there is a particular need for such methods and systems.

SUMMARY OF THE INVENTION

According to one aspect of the present invention there is provided an apparatus for compressing a gas, including a fixed-volume container having a hollow and a moveable element subdividing the hollow into a first variable-volume portion and a second variable-volume portion, the second variable-volume portion having an opening for introducing therein a hydraulic and/or pneumatic fluid under pressure, for causing an increase in the volume of the second variable-portion by moving the moveable element, thereby, consequently, decreasing the volume of the first variable-volume portion and compressing a gas contained therein.

According to further features in preferred embodiments of the invention described below, the first variable-volume portion is designed and constructed so as to be couplable during a first phase of operation to a mechanism for introducing a gas into the first variable-volume portion, and to be couplable during a second phase of operation to a mechanism for transporting a compressed gas from the first variable-volume portion to a compressed gas utilizing application, for supplying a compressed gas to said compressed gas utilizing application.

According to still further features in the described preferred embodiments, the first variable-volume portion is coupled during the first phase of operation to a source of a gas, and is coupled during a second phase of operation to a mechanism for transporting a compressed gas from the first variable-volume portion to a compressed gas utilizing application.

According to still further features in the described preferred embodiments, the second variable-volume portion is designed and constructed to be couplable during the second phase of operation to a source of hydraulic and/or pneumatic fluid under pressure.

According to still further features in the described preferred embodiments, the second variable-volume portion is coupled during the second phase of operation to a source of hydraulic and/or pneumatic fluid under pressure.

According to still further features in the described preferred embodiments, the moveable element is constructed of a rigid material.

According to still further features in the described preferred embodiments, the moveable element is a piston.

According to still further features in the described preferred embodiments, the moveable element is at least partially constructed of a flexible material, such as an elastomer, or a reinforced rubber.

According to still further features in the described preferred embodiments, the moveable element is a diaphragm.

According to still further features in the described preferred embodiments, the moveable element is a bladder. The first variable-volume portion forms a portion of said hollow and may be defined by the bladder, or it may be defined by the fixed volume container and outside the bladder.

According to another aspect of the present invention there is provided a method for compressing a gas, utilizing a fixed-volume container having a hollow and a moveable element subdividing the hollow into a first variable-volume portion and a second variable-volume portion, including the steps of introducing a gas into the first variable-volume portion of the hollow during a first phase of operation; and introducing a hydraulic and/or pneumatic fluid under pressure into the second variable-volume portion of the hollow during a second phase of operation, thereby increasing the volume of the second variable-volume portion by moving the moveable element, thereby, consequently decreasing the volume of the first variable-volume portion and compressing the gas contained therein.

According to yet another aspect of the present invention there is provided a method for supplying a compressed gas to a compressed gas utilizing application, utilizing a fixed-volume container having a hollow and a moveable element subdividing the hollow into a first variable-volume portion and a second variable-volume portion, including the steps of introducing a gas into the first variable-volume portion of the hollow during a first phase of operation; introducing a hydraulic and/or pneumatic fluid under pressure into the second variable-volume portion of the hollow during a second phase of operation, thereby increasing the volume of the second variable-volume portion by moving the moveable element, thereby consequently decreasing the volume of the first variable-volume portion and compressing the gas contained therein, and transferring a gas during the second phase of operation from the first variable-volume portion of the hollow to the compressed gas utilizing application.

According to still another aspect of the present invention there is provided a compressed gas utilization system including a first gas compression apparatus for compressing a gas, including a fixed-volume container having a hollow and a moveable element subdividing the hollow into a first variable-volume portion and a second variable-volume portion, the second variable-volume portion having an opening for introducing therein a hydraulic and/or pneumatic fluid under pressure, for causing an increase in the volume of the second variable-volume portion by moving the moveable element, thereby consequently decreasing the volume of the first variable-volume portion and compressing a gas contained therein, the system further including a compressed gas utilizing application utilizing compressed gas, and a first mechanism for transporting a compressed gas from the first variable-volume portion of the first gas compression apparatus to the compressed gas utilizing application.

According to further features in preferred embodiments of the invention described below, the first variable-volume portion of the first gas compression apparatus is coupled during a first phase of operation to a mechanism for introducing a gas into the first variable-volume portion of the first gas compression apparatus, and the first variable-volume portion of the first gas compression apparatus is coupled during a second phase of operation to the mechanism for transporting a compressed gas from the first variable-volume portion of the first gas compression apparatus to the compressed gas utilizing application.

According to still further features in the described preferred embodiments, the system further includes a second gas compression apparatus including a fixed-volume container having a hollow and a moveable element subdividing the hollow into a first variable-volume portion and a second variable-volume portion, the second variable-volume portion having an opening for introducing therein a hydraulic and/or pneumatic fluid under pressure, for causing an increase in the volume of the second variable-volume portion by moving the moveable element, thereby consequently decreasing a volume of the first variable-volume portion and compressing a gas contained therein, and further includes a second mechanism for transporting a compressed gas from the first variable-volume portion of the second gas compression apparatus to the compressed gas utilizing application.

According to still further features in the described preferred embodiments, the system is designed and constructed so as to enable the first gas compression apparatus to be in the first phase of operation while the second gas compression apparatus is in the second phase of operation, and the first gas compression apparatus to be in the second phase of operation while the second gas compression apparatus is in the first phase of operation.

According to still further features in the described preferred embodiments, the system is designed and constructed so that the first gas compression apparatus is in the first phase of operation when the second gas compression apparatus is in the second phase of operation, and the first gas compression apparatus is in the second phase of operation when the second gas compression apparatus is in the first phase of operation.

According to an additional aspect of the present invention there is provided a cryosurgery system including a first gas compressor for compressing gas, a cryoablation apparatus utilizing compressed gas, and a mechanism for transporting compressed gas from the gas compressor to the cryoablation apparatus during use.

According to further features in the described preferred embodiments, the cryoablation apparatus includes a Joule-Thomson heat exchanger for cooling a portion of the cryoablation apparatus.

According to still further features in the described preferred embodiments, the system includes a mechanism for re-pressurizing a gas depressurized by use in the Joule-Thomson heat exchanger.

According to still further features in the described preferred embodiments, the system further includes a mechanism for transporting a gas depressurized by use in a Joule-Thomson heat exchanger from the cryoablation apparatus to the gas compressor. The mechanism may include a second gas compressor, and may also include a gas reservoir.

According to still further features in the described preferred embodiments, the first gas compressor includes a fixed-volume container having a hollow and a moveable element subdividing the hollow into a first variable-volume portion and a second variable-volume portion, the second variable-volume portion having an opening for introducing therein a hydraulic and/or pneumatic fluid under pressure, for causing an increase in a volume of the second variable-volume portion by moving the moveable element, thereby consequently decreasing a volume of the first variable-volume portion and compressing a gas contained therein.

According to still further features in the described preferred embodiments, the first variable-volume portion of the first gas compression apparatus is coupled during a first phase of operation to a mechanism for introducing a gas into the first variable-volume portion of the first gas compression apparatus, and the first variable-volume portion of the first gas compression apparatus is coupled during a second phase of operation to the mechanism for transporting a compressed gas from the first variable-volume portion of the first gas compression apparatus to the compressed gas utilizing application.

According to yet an additional aspect of the present invention there is provided a method for cryosurgery, involving in situ compression of gas, including using a first in situ gas compressor to compress a gas, thereby transforming the gas into a first compressed gas at a first gas pressure, transferring the first compressed gas at the first gas pressure from the first gas compressor to a cryoablation apparatus utilizing the first compressed gas at the first gas pressure; and using the cryoablation apparatus to perform cryoablation, thereby creating a decompressed gas at a second gas pressure.

According to further features in the described preferred embodiments, the method further includes the steps of transferring the depressurized gas at the second gas pressure to the first gas compressor, for recompression and reuse, and recompressing and reusing the depressurized gas.

According to still further features in the described preferred embodiments, the method further includes the steps of transferring said depressurized gas at the second gas pressure to a second gas compressor, for recompression and reuse, and recompressing and reusing the depressurized gas.

The present invention successfully addresses the shortcomings of the presently known configurations by providing a method and apparatus for compressing gas which does not depend on a rapidly moving reciprocating piston system, and therefore does not require lubrication which might contaminate the purity of the compressed gas.

The present invention further successfully addresses the shortcomings of the presently known configurations by providing a method and apparatus for supplying gas of substantially constant pressure to a compressed-gas application, using standard cylinders of compressed gas as a source of gas.

The present invention further successfully addresses the shortcomings of the presently known configurations by providing a method and apparatus for supplying gas of high pressure to an application using high-pressure compressed gas, utilizing standard cylinders of moderate pressure compressed gas as a source of gas. In particular, the present invention successfully addresses the shortcomings of the presently known configurations of cryosurgery systems by providing a method and apparatus for cryoablation that efficiently uses gas for Joule-Thomson cooling (or heating) from a gas source whose initial pressure is lower than that required for efficient operation of a Joule-Thomson device, and is in the range of gas pressures available from standard industrial gas sources. This is in sharp distinction to methods of prior art, which require specialized high-pressure gas sources for operation of a cryosurgery device.

The present invention further successfully addresses the shortcomings of the presently known configurations by providing a method and apparatus for supplying gas of high pressure while nevertheless utilizing substantially most or all of the compressed gas supplied in standard compressed gas cylinders. In particular, the present invention successfully addresses the shortcomings of the presently known configurations of cryosurgery systems by providing a method and apparatus for cryoablation in which substantially most of the cooling gasses supplied in a tank of cooling gas can be used for cooling a cryoprobe, and substantially most of the heating gasses supplied in a tank of heating gas can be used for heating a cryoprobe. This is in distinction to methods of prior art wherein a substantial portion of the contents of each tank of cooling gas cannot be used for cooling a cryoprobe, and a substantial portion of the contents of each tank of heating gas cannot be used for used for heating a cryoprobe.

The present invention further successfully addresses the shortcomings of the presently known configurations by providing a method and apparatus for re-pressurizing and reusing gas supplied from a high-pressure source and depressurized by utilization in an application. In particular, the present invention successfully addresses the shortcomings of presently known configurations of cryosurgery systems by providing a method and apparatus for the practical and economical use of rare and expensive gasses in such systems through the use of method and apparatus for re-pressurizing and reusing such gasses.

BRIEF DESCRIPTION OF THE DRAWINGS

The invention is herein described, by way of example only, with reference to the accompanying drawings. With specific reference now to drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
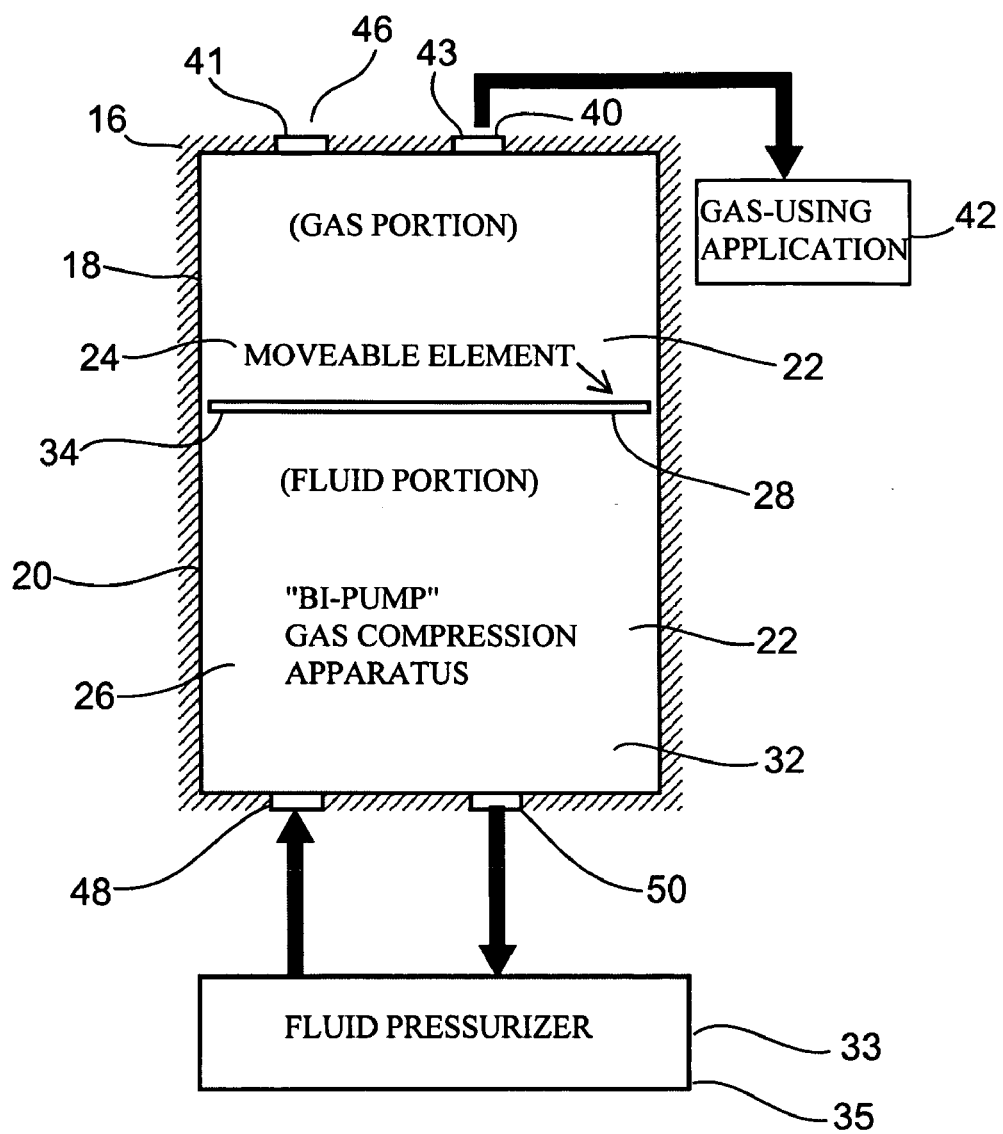
FIG. 1 is a gas compression apparatus utilizing a piston, according to the present invention.

The present invention is of apparatus and method for compressing and/or re-compressing gas which can be used for in situ gas compression as a method of supplying compressed gas to a compressed gas utilizing application, such as a cryoablation apparatus. More specifically, the present invention can be used to compress a gas for use in a compressed gas utilizing application. The present invention can further be used to raise the pressure of a compressed gas, to thereby supply high pressure gas to a compressed gas utilizing application using medium pressure gas sources. It can further be used to supply compressed gas at a constant selected pressure to a compressed gas utilizing application. It can further be used to supply compressed gas to a compressed gas utilizing application, while utilizing all or substantially most of the gas supplied in conventional gas cylinders or similar containers.

In one particular and presently preferred embodiment, the present invention is used to supply high pressure gas to a cryosurgery apparatus and enables re-pressurization and reuse of a compressed gas used in a Joule-Thomson heat exchanger for heating and cryogenic cooling.

To enhance clarity of the following descriptions, the following terms and phrases will first be defined:

The terms "compression" and "pressurization" are used herein interchangeably. A "compressed gas" is a pressurized gas, a gas held under a pressure higher than atmospheric pressure.

A "compressed gas utilizing application" is a device, apparatus, or system utilizing compressed gas while operating.

The phrase "medium pressure" is used herein to refer to a degree of pressurization in or near the range of pressurization typical of gasses sold by industrial supply sources when supplying gasses used for common industrial purposes. By way of example, compressed argon is commonly sold by industrial supply sources pressurized to about 2500 PSI. It is noted that other particular types of gasses may be typically available in other pressure ranges. The term "medium pressure", as used herein, is not limited to a particular pressure, but is used generally to refer to a pressure range typically commercially available for each type of gas, and is contrasted with "high pressure" defined hereinbelow.

The phrase "high pressure" is used herein to refer to a degree of pressurization higher than the range of pressurization typical of gasses sold by industrial supply houses when supplying gasses used for common industrial purposes. By way of example, compressed argon used in cryosurgery apparatus is typically pressurized to the range of 3000-4500 PSI, which range, for argon, is referred to herein as a high pressure, and argon gasses at such pressure are referred to herein as high pressure gasses. The term "high pressure" as used herein is not, however, limited to that particular pressure range. Rather, the term "high pressure" is used herein to refer to that pressure which, for any particular type of gas, is higher than the "medium pressure" at which that particular type of gas is typically easily and economically commercially available.

The phrase "low pressure" is used herein to refer to a degree of pressurization lower than the range of pressurization typical of gasses sold for use in compressed gas utilizing applications. A gas may be at "low pressure", and yet be at a pressure higher than atmospheric pressure.

The phrase "depressurized gas" and the term "depressurization" are used herein to refer particularly to the pressurization state of a gas which has been used by a compressed gas utilizing application, and which is consequently at a low pressure subsequent to having been so used.

The phrase "Joule-Thomson heat exchanger" refers, in general, to any device used for cryogenic cooling or for heating, in which a gas is passed from a first region of the device, wherein it is held under higher pressure, to a second region of the device, wherein it is enabled to expand to lower pressure. Such devices are also commonly referred to as Joule-Thomson devices. A Joule-Thomson heat exchanger may be a simple conduit, or it may include an orifice through which gas passes from the first, higher pressure, region of the device to the second, lower pressure, region of the device. The expansion of certain gasses (referred to herein as "cooling gasses") in a Joule-Thomson heat exchanger, when passing from a region of higher pressure to a region of lower pressure, causes these gasses to cool and may cause them to liquefy, creating a cryogenic pool of liquefied gas. This process cools the Joule-Thomson heat exchanger itself, and also cools any thermally conductive materials in contact therewith. The expansion of certain other gasses (referred to herein as "heating gasses") in a Joule-Thomson heat exchanger causes the gasses to heat, thereby heating the Joule-Thomson heat exchanger itself and also heating any thermally conductive materials in contact therewith.

The principles and operation of a gas compression apparatus and of a compressed gas utilization system according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 presents a preferred embodiment of a gas compression apparatus according to the present invention. For convenience and clarity, a gas compression apparatus according to the present invention will be referred to hereinbelow as a "bi-pump" 18.

In FIG. 1, bi-pump 18 comprises a container 20, rigidly constructed of a strong material such as a metal and designed to withstand high pressures. Container 20 is optionally surrounded by a thermally insulating layer 16. Container 20 has a hollow 22 and a moveable element 28. Moveable element 28 serves to divide hollow 22 into a first variable-volume portion, referred to herein as gas portion 24, and a second variable-volume portion, referred to herein as fluid portion 26.

Gas portion 24 is for receiving, holding, and compressing a gas. A gas to be compressed is introduced into gas portion 24 through a gas input coupling 46. Gas input coupling 46 is for coupling bi-pump 18 to a source of gas which is to undergo compression. The input gas introduced into bi-pump 18 may be an uncompressed gas, or may be a pressurized gas at a pressure lower than a pressure which is desired to be obtained, e.g., for use in a compressed gas utilizing application 42. A gas output coupling 40 is provided for coupling gas portion 24 to compressed gas utilizing application 42, or to some other destination for the compressed gas. Thus, compressed gas may be transferred to compressed gas utilizing application 42 or to any other destination through gas output coupling 40. Optionally, gas input coupling 46 includes a gas input valve 41 for controlling flow of input gas. Optionally, gas output couping 40 includes a gas output valve 43 for controlling flow of output gas.

The gas introduced into gas portion 24 can be any gas, including, but not limited to argon, nitrogen, air, krypton, $CF_4$, $N_2O$, $CO_2$, and helium.

Fluid portion 26 is for receiving and holding a pressurizing fluid 32. Pressurizing fluid 32 enters fluid portion 26 through a pressurizing fluid input coupling 48, and can be drained from the apparatus through pressurizing fluid output coupling 50.

During a first phase of operation, a gas is introduced into gas portion 24 through input gas coupling 46. Also during the first phase of operation, pressurizing fluid 32 present in fluid portion 26 as a result of previous iterations of the process is allowed to drain from fluid portion 26 through pressurizing fluid output coupling 50.

During a second phase of operation, pressurizing fluid 32 is introduced into fluid portion 26 in order to exert pressure on moveable element 28. Pressurizing fluid 32 is any fluid capable of exerting such pressure, such as a hydraulic fluid such as oil or water, or such as a pneumatic fluid such as a compressed gas, or such as a mixture of a hydraulic fluid such as oil mixed with a pneumatic fluid such as a compressed gas. Use of a hydraulic liquid as pressurizing fluid 32 is the currently preferred choice in preferred embodiments of the invention.

During a second phase of operation, fluid pressurizer 33 supplies pressurizing fluid 32 under pressure. Pressurized pressurizing fluid 32 is introduced into fluid portion 26 through pressurizing fluid input coupling 48. In a preferred embodiment, fluid pressurizer 33 is a hydraulic unit 35, capable of supplying a hydraulic liquid at a selected pressure, according to methods well known in the art. Pressurizing fluid 32 exerts pressure on moveable element 28, causing moveable element 28 to move.

The movement of moveable element 28 in response to pressure exerted by pressurizing fluid 32 causes the volume of fluid portion 26 of hollow 22 to increase. Gas portion 24 and fluid portion 26 share the same fixed total volume, which is the volume of hollow 22 exclusive of the volume of moveable element 28, which in preferred embodiments is relatively non-compressible.

Consequently, an increase in the volume of fluid portion 26 coincides with a decrease in the volume of gas portion 24. Thus, the movement of moveable element 28 forces the gas contained in gas portion 24 into a smaller volume, and the gas is thereby compressed proportionally.

Moreover, moveable element 28 moves relatively freely, hence moveable element 28 will tend to move in such a manner as to equalize pressure between gas portion 24 and fluid portion 26. In consequence, changes in pressure of pressurizing fluid 32 as supplied by fluid pressurizer 33 are rapidly reflected as corresponding changes in pressure of the gas being compressed within gas portion 24. Thus, pressure of gas compressed in gas portion 24 is substantially controlled by pressure of pressurizing fluid 32. Fluid pressurizer 33 is capable of supplying fluid at a selected pressure, using techniques well known to one schooled in the art. Control of output pressure of fluid pressurizer 33 constitutes control of pressure of gas compressed by gas portion 24. Thus, bi-pump 18 can compress gas to a selected and controlled pressurize.

Thus, according to another aspect of the present invention there is provided a method for compressing a gas, utilizing a fixed-volume container having a hollow and a moveable element subdividing the hollow into a first variable-volume portion and a second variable-volume portion. The method according to this aspect of the invention is effected by introducing a gas into the first variable-volume portion of the hollow during a first phase of operation; and thereafter introducing a hydraulic or pneumatic fluid under pressure into the second variable-volume portion of the hollow during a second phase of operation, thereby increasing a volume of the second variable-volume portion by moving the moveable element, thereby, consequently decreasing a volume of the first variable-volume portion and compressing the gas contained therein.

According to methods of use in currently preferred embodiments of the present invention, during a second phase of operation, compressed gas from gas portion 24 is allowed to pass through gas output coupling 40, from where it can serve as a supply of compressed gas to compressed gas utilizing application 42 or other needs.

Gas input coupling 46 and gas output coupling 40 are shown as different couplings, yet in an optional construction they may be a combined input/output gas coupling. Similarly, pressurizing fluid input coupling 48 and pressurizing fluid output coupling 50 are shown as different couplings, yet in an optional construction they may be a combined pressurizing fluid input/output coupling.

Moveable element 28 will either move rigidly, changing position within container 20, or else it will move elastically, changing shape. An example of rigid movement is presented by the embodiment of FIG. 1. Examples of elastic movement are given by the embodiments presented by FIGS. 2, 3 and 4.

In a preferred embodiment of the present invention, specifically shown in FIG. 1, moveable element 28 is constructed of a rigid material, such as a metal or a hard non-deformable polymeric material or composite material. In this preferred embodiment container 20 is cylindrical, and moveable element 28 is designed and constructed in the form of a piston 34. Piston 34 is able to move longitudinally within cylindrical container 20. During a second phase of operation, when pressurized pressurizing fluid 32 is introduced into fluid portion 26 it exerts pressure on piston 34. Piston 34 responds to the pressure by moving longitudinally in container 20 towards gas portion 24. The volume of gas portion 24 is thereby reduced and the gas contained therein is compressed.

Figure 2:
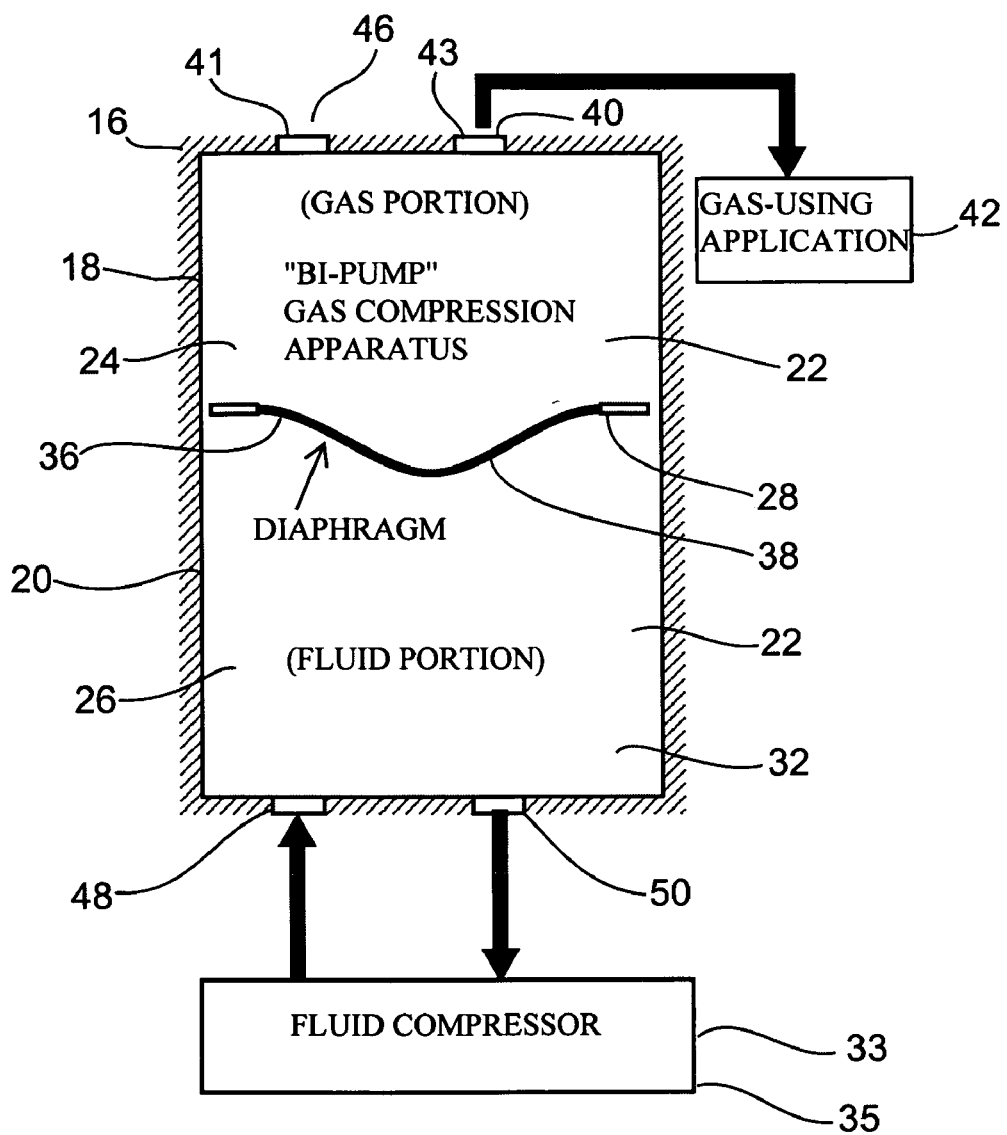
FIG. 2 is a gas compression apparatus utilizing a diaphragm, according to the present invention.
Figure 3:
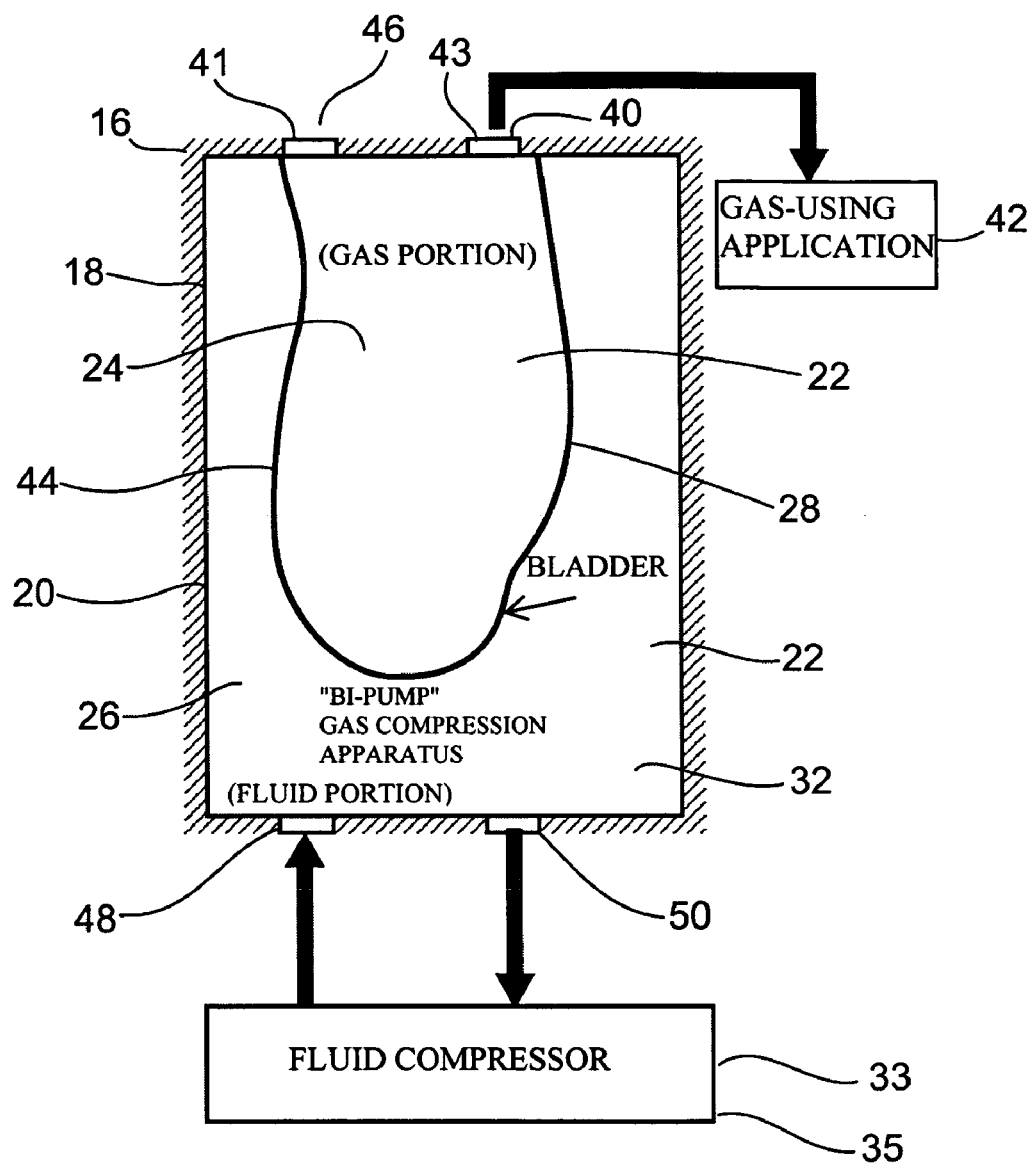
FIG. 3 is a gas compression apparatus utilizing a bladder, according to the present invention.
Figure 4:
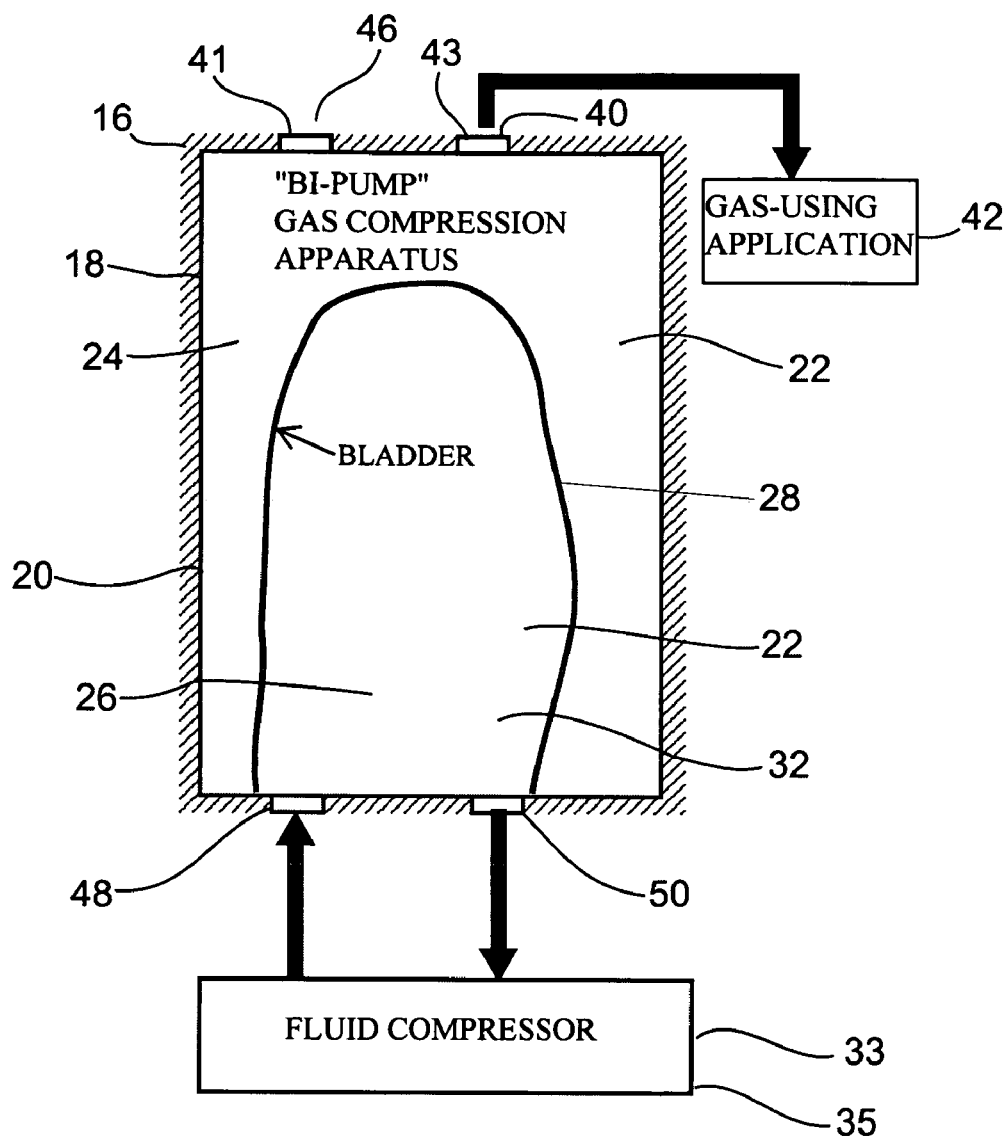
FIG. 4 is an alternative construction of a gas compression apparatus utilizing a bladder, according to the present invention.

FIGS. 2, 3 and 4 present preferred embodiments in which at least a part of moveable element 28 is constructed of flexible material, such as a reinforced rubber or an elastomer.

In a preferred embodiment of the present invention shown in FIG. 2, moveable element 28 is a diaphragm 36. Diaphragm 36 is anchored at a fixed in position within container 20, yet flexible area 38 of diaphragm 36 is constructed of an elastic material. During the second phase of operation, high-pressure pressurizing fluid 32 is introduced into fluid portion 26. Pressure exerted by pressurizing fluid 32 on diaphragm 36 causes flexible area 38 of diaphragm 36 to distend towards gas portion 24. The volume of gas portion 24 is thereby reduced and the gas contained therein is compressed.

In preferred embodiments of the present invention shown in FIGS. 3 and 4, moveable element 28 is a bladder 44. Bladder 44 is preferably constructed of a strong but very flexible material, and has a shape something similar to the shape of a child's balloon. At its maximum expansion, bladder 44 extends to fill substantially all of the volume of hollow 22. At its minimum expansion, bladder 44 takes up little more volume than the volume of the materials of which bladder 44 is composed. In a preferred embodiment the volume of bladder 44 at minimum expansion is typically approximately 15% of the volume of hollow 22.

In a preferred embodiment of the present invention shown in FIG. 3, gas portion 24 is the interior volume of bladder 44 and fluid portion 26 is the volume within hollow 22 of container 20 which is outside of bladder 44. During the first phase of operation, gas is introduced into the interior of bladder 44 through gas input coupling 46. During the second phase of operation pressurizing fluid 32 is introduced into the volume within hollow 22 of container 20 which is outside bladder 44. Pressure exerted by pressurizing fluid 32 on bladder 44 causes bladder 44 to contract, thereby exerting pressure on gas contained within bladder 44, and consequently compressing it.

In a preferred embodiment of the present invention shown in FIG. 4, gas portion 24 is the volume within hollow 22 of container 20 which is outside of bladder 44. In this embodiment, fluid portion 26 is the interior volume of bladder 44. During the first phase of operation gas is introduced into the portion of hollow 22 which is exterior to bladder 44, through gas input coupling 46, causing bladder 44 to collapse. During the second phase of operation pressurizing fluid 32 is introduced into the interior volume of bladder 44. Pressure exerted by pressurizing fluid 32 on the interior of bladder 44 causes bladder 44 to expand. Since gas portion 24 is the volume of hollow 22 exterior to bladder 44, expansion of bladder 44 causes a reduction of volume of gas portion 24, thereby compressing a gas therein.

It is to be noted that a configuration reversed with respect to those presented in FIG. 3 and in FIG. 4 is known in prior art, yet according to the teachings of the prior art the configuration is used to fulfill quite a different function. A device known in the art as an "accumulator" is used to pressurize a liquid, such as a hydraulic liquid, e.g., water or oil. An example is provided by the accumulator sold by Accumulators Inc. of 9042 Long Point Road, Huston Tex. 77055, part number A56100, or that sold by Ballas Engineering & Mechanization Ltd. of 4 HaManor Street, Tel Aviv, Israel, and identified by part number SB800/1000. The function of this accumulator, and of all know usages of "accumulators" of similar design, according to the teachings of the prior art, is to pressurize a hydraulic liquid. For this purpose, a compressed gas is used. In other words, the usage of an accumulator according to the prior art is just the reverse of the usage presented herein. In a prior art accumulator, gas is introduced under pressure into a portion of the device, for the purpose of exerting a force on an extensible bladder in order to pressurize a liquid such as a hydraulic liquid like water or oil, which is then subsequently used in an application requiring a pressurized hydraulic liquid for operation. This is, of course, in sharp contrast to the configuration, purpose, and usages of the present invention, wherein a pressurizing fluid is used to compress a gas for use by a compressed gas utilizing application.

An advantage of an apparatus constructed in accordance with the teachings of the present invention is in the ability of the apparatus to supply gas at a constant and selected pressure. In each of the embodiments presented in FIGS. 1-4, pressure of a compressed gas held under pressure in gas portion 24 will, during the second phase of operation, be substantially similar to pressure exerted by pressurizing fluid 32 on moveable element 28. In a preferred mode of operation, pressurizing fluid 32 is supplied by fluid pressurizer 33 through pressurizing fluid input coupling 48 at a constant pressure chosen to be an optimal pressure for a selected gas application. Bi-pump 18 is thus enabled to supply compressed gas to compressed gas utilizing application 42 at a substantially constant and optimized pressure. This is in sharp contrast to the configurations of prior art, in which compressed gas is typically supplied to compressed gas utilizing applications in the form of compressed gas containers, such as cylinders, of constant geometry. In such configurations, the pressure of compressed gas supplied to the application typically depends on the amount of gas remaining in the supplied container of gas. That pressure varies over time, pressure in the gas supply containers gradually falling as gas in the container is gradually used by the compressed gas utilizing application.

For some compressed gas utilizing applications, for example for the cryosurgery application discussed more fully hereinbelow, it is advantageous, for efficient operation of the application, to have a supply of compressed gas at a substantially constant pressure. Thus, the ability of a gas compression apparatus according to the present invention to supply compressed gas to a compressed gas utilizing application at a substantially constant and optimized pressure is an important advantage of the present invention over the configurations of the prior art.

An additional advantage of an apparatus according to the present invention lies in the ability of the apparatus to utilize, during the second phase of operation, substantially all of the gas supplied to gas portion 24 during the first phase of operation. Since the pressure of compressed gas supplied to compressed gas utilizing application 42 through gas output connector 40 is not dependent on the amount of gas remaining in the apparatus, the second phase of operation can be continued until substantially all of the gas present in gas portion 24 has been transferred through gas output coupling 40 to compressed gas utilizing application 42. This is in sharp contrast to the typical situation of prior art, wherein the pressure of gas supplied in a gas cylinder or similar container gradually falls over time as gas is used. In such a system a point is reached at which the pressure of the gas supplied falls below the minimum pressure required by compressed gas utilizing application 42. At that point the gas supply container must typically be returned for refilling by a supplier, despite the fact that a significant amount of valuable gas is still contained in the container. In a cryosurgery system, for example, the required gas pressure is typically so high that gas supply cylinders used by conventional cryosurgery systems are typically returned to a supplier for refilling with more than half the supplied gas still in the cylinder.

Figure 5:
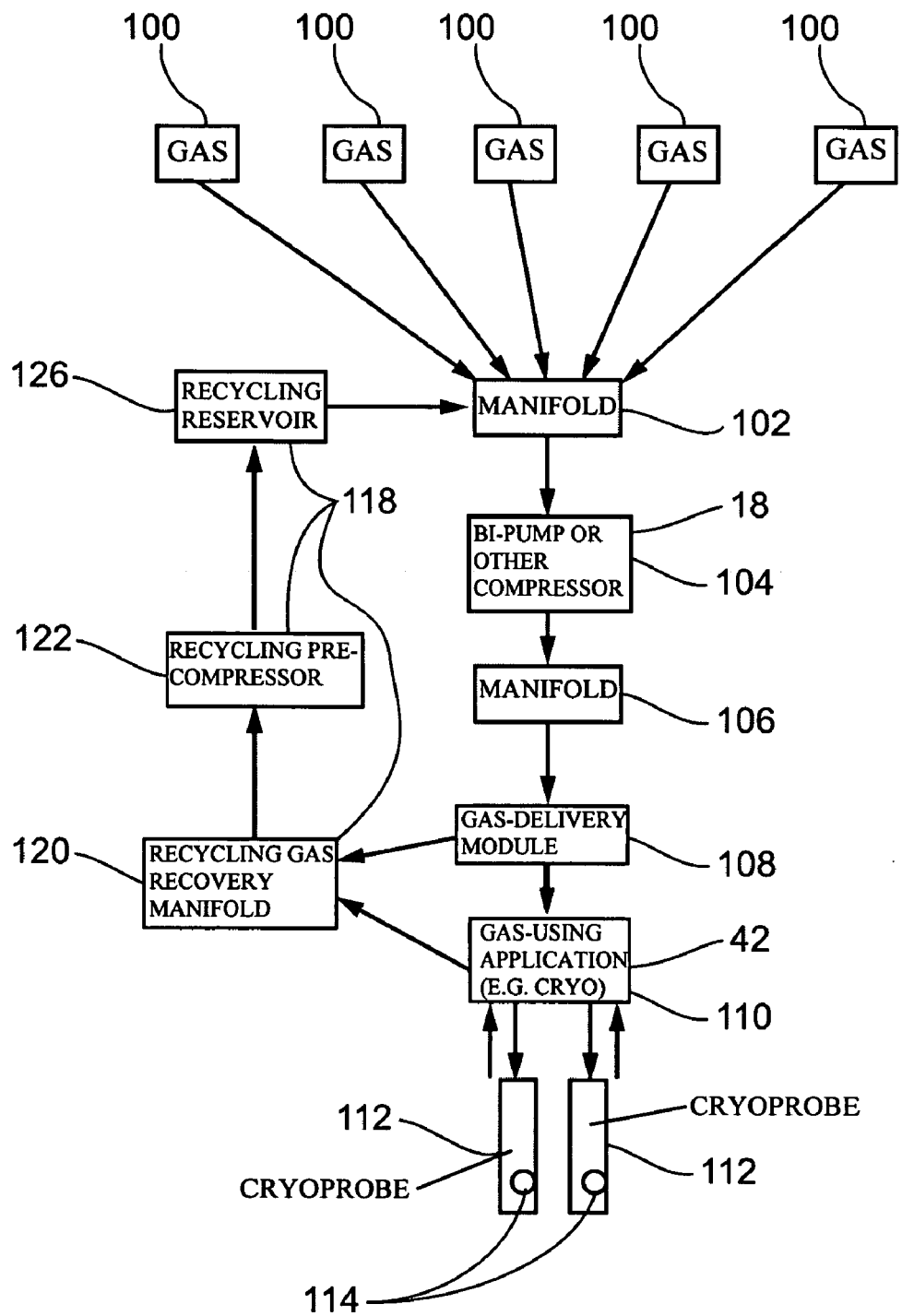
FIG. 5 is an exemplary compressed gas utilization system in the form of a cryosurgery apparatus utilizing in situ compressed gas, according to the present invention.

FIG. 5 presents a compressed gas utilization system according to the present invention.

At least one gas source 100 supplies gas to an input gas manifold 102. Gas from input gas manifold 102 is compressed by gas compression apparatus 104, then passes through an optional compressed gas manifold 106 to a compressed gas delivery module 108. In a preferred embodiment, compressed gas delivery module 108 is a control module for controlling delivery of compressed gas to compressed gas utilizing application 42, which utilizes the compressed gas.

Gas source 100 is a source of any gas. In a preferred embodiment of the present invention, a plurality of gas sources 100 are enabled to input gas to input gas manifold 102.

Gas source 100 may be a source of uncompressed gas, such as air. Gas source 100 may also be a source of compressed gas at a low pressure, at a medium pressure, or at a high pressure. In a preferred embodiment, gas sources 100 typically supply gas at a pressure lower than a pressure desired for a particular compressed gas utilizing application 42. Examples of compressed gas sources 100 include an industrial 'always on' compressed gas supply line, an external gas cylinder or similar gas container, a plurality of external gas cylinders or similar gas containers, an internal gas cylinder or similar gas container, and a plurality of internal gas cylinders or similar gas containers.

Gas from gas sources 100 is supplied through input gas manifold 102 to gas compression apparatus 104. Gas compression apparatus 104 is for raising the pressure of a gas from a first pressure, the gas pressure supplied by gas sources 100, to a second pressure, a pressure appropriate for use by compressed gas utilizing application 42. In a preferred embodiment, gas compression apparatus 104 is a bi-pump 18, described hereinabove.

Compressed gas from gas compression apparatus 104 passes through optional compressed gas manifold 106 to compressed gas delivery module 108, which controls delivery of compressed gas to compressed gas utilizing application 42, where it is used.

An optional gas recycling module 118 is for recycling gas that is depressurized in consequence of having been utilized by compressed gas utilizing application 42. Decompressed gas is recovered from compressed gas utilizing application 42 or from compressed gas delivery module 108 to a gas recovery manifold 120. Gas from gas recovery manifold 120 may optionally be repressurized or partially repressurized by an optional recycling gas pre-compressor 122, and may further optionally be stored in a recovered gas reservoir 126. The recovered and repressurized gas is ultimately transported or guided to compressed gas utilizing application 42, where it is re-used. In a preferred embodiment of the present invention presented in FIG. 5, the recovered gas, after optional pre-compression by recycling gas pre-compressor 122 and optional intermediate storage in recovered gas reservoir 126, is ultimately transported or guided to input gas manifold 102 for further repressurization by gas compression apparatus 104, whence it is supplied for re-use by compressed gas utilizing application 42.

A preferred embodiment of a compressed gas utilization system according to the present invention, wherein compressed gas utilizing application 42 is a cryosurgery application 110, constitutes a departure from prior art, and presents several advantages over prior art configurations using compressed gas for cooling portions of a cryosurgery apparatus.

Referring again to FIG. 5, compressed gas utilizing application 42 is cryosurgery application 110, in which compressed gas is supplied to at least one cryoprobe 112, preferably a plurality of cryoprobes 112. Cryoprobes 112 utilize compressed gas in Joule-Thomson heat exchangers 114 for cooling and optionally also for heating cryoprobes 112. In a preferred embodiment, compressed cooling gasses are supplied to cryosurgery application 110 to cool cryoprobes 112, generally to affect cryoablation of tissues, and compressed heating gasses are supplied to cryosurgery application 110 to heat cryoprobes 112, generally to melt frozen tissues touching cryoprobes 112 so as to facilitate the disengagement of cryoprobes 112 from body tissues subsequent to cryoablation. In a preferred embodiment, gas decompressed by utilization in cryoprobes 112 is conducted, either directly or by way of application 42, to gas recovery manifold 120, for recompression and reuse as described hereinabove.

Prior art cryosurgery systems participate in the disadvantages of high pressure gas systems recited hereinabove. These disadvantages include the expense and inconvenience of acquiring high pressure gas for use in the systems, an inability to utilize substantially most of the high pressure gas supplied in high pressure gas cylinders or other gas containers, and the expense and wastefulness of systems which vent expensive gasses to the atmosphere after a single use.

A compressed gas utilization system according to the present invention, wherein compressed gas utilizing application 42 is cryosurgery application 110, overcomes these and other advantages of prior art systems.

Cryosurgery applications typically require high pressure gas for effective heating and cooling of cryoprobes 112. Argon, for example, is often used as a compressed gas for cryosurgery applications, and is optimally used at pressures in the range of 3000-4500 PSI. Industrial supply sources of compressed argon typically supply compressed argon at pressures of about 2500 PSI. Thus, a preferred embodiment of a compressed gas utilization system of the present invention enables to use argon gas compressed to medium pressure, which can conveniently be purchased from standard industrial sources, as a gas source 100, yet supplies high pressure argon to a compressed gas utilizing application 42 such as a cryosurgery application 110. This ability constitutes a significant improvement over prior art.

In another preferred embodiment, also including a cryosurgery application 110 utilizing cryoprobes 112, krypton gas is used as the compressed gas. Use of krypton gas instead of argon enables efficient cooling of cryoprobes 112 at lower pressures than those required for efficient cooling utilizing argon gas. Krypton gas enables efficient cooling at pressures in the neighborhood of 2,500 PSI, considerably lower than the pressures required for argon. Consequently, cryosurgery systems designed and constructed to be used with compressed krypton rather than compressed argon present various advantages, including relatively simplicity of construction and convenience of use.

In prior art cryosurgery systems compressed gas used for cooling a cryoprobe is typically subsequently vented to atmosphere rather than being recovered and recycled. Krypton gas, however, is expensive, and cannot be conveniently and economically used in such a prior art system. Thus a preferred embodiment of a compressed gas utilization system according to the present invention, wherein compressed gas utilizing application 42 is cryosurgery application 110, the embodiment further incorporating optional gas recycling module 118, enables efficient and economical use of compressed krypton in a cryosurgery application, thereby constituting a further significant improvement over prior art.

Thus, according to another aspect of the present invention there is provided a method for cryosurgery involving in situ compression of gas. The method according to this aspect of the invention is effected by using a first in situ gas compressor to compress a gas, thereby transforming the gas into a first compressed gas at a first gas pressure, transferring the first compressed gas at the first gas pressure from the first gas compressor to a cryoablation apparatus which utilizes the first compressed gas at the first gas pressure, and using the cryoablation apparatus to perform cryoablation.

According to yet another aspect of the present invention there is provided a method for cryosurgery, involving in situ compression of gas and further providing for re-compression and re-utilization of the gas. The method according to this aspect of the invention is effected by using a first in situ gas compressor to compress a gas, thereby transforming the gas into a first compressed gas at a first gas pressure, transferring the first compressed gas at the first gas pressure from the first gas compressor to a cryoablation apparatus which utilizes the first compressed gas at the first gas pressure, using the cryoablation apparatus to perform cryoablation, thereby creating a decompressed gas at a second gas pressure, transferring the depressurized gas at the second gas pressure either to the first gas compressor or to a second gas compressor for recompression and reuse, and recompressing and reusing the depressurized gas.

Still further advantages of a compressed gas utilization system according to the present invention may be particularly noted in preferred embodiments wherein gas compression apparatus 104 is a bi-pump 18, bi-pump 18 being a gas compression apparatus according to the present invention.

Use of bi-pump 18 enables to supply compressed gas at a continuous, even, selected pressure to compressed gas utilizing application 42, irrespective of pressure levels in gas sources 100. Use of bi-pump 18 further enables utilizing all or substantially most of a gas supplied in internal or external gas cylinders or other containers used as gas sources 100. Use of bi-pump 18 presents the further advantage that bi-pump 18 is not a rapidly reciprocating pump, therefore requires no lubrication and does not risk contamination of compressed gas by volatile lubricating materials.

Thus, according to another aspect of the present invention there is provided a method for supplying a compressed gas to a compressed gas utilizing application, utilizing a fixed-volume container having a hollow, and a moveable element subdividing the hollow into a first variable-volume portion and a second variable-volume portion. The method according to this aspect of the invention is effected by introducing a gas into the first variable-volume portion of the hollow during a first phase of operation, then introducing a hydraulic and/or pneumatic fluid under pressure into the second variable-volume portion of the hollow during a second phase of operation, thereby increasing a volume of the second variable-volume portion by moving the moveable element, thereby consequently decreasing a volume of the first variable-volume portion and compressing a gas contained therein, and transferring the compressed gas during the second phase of operation from the first variable-volume portion of the hollow to a compressed gas utilizing application.

Compressed gas delivery module 108 may include various mechanisms such as valves, one-way valves, pressure re, dryers, filters and measuring devices for temperature and pressure, for managing the delivery of compressed gas to compressed gas utilizing application 42, according to methods well known in the art.

Figure 6:
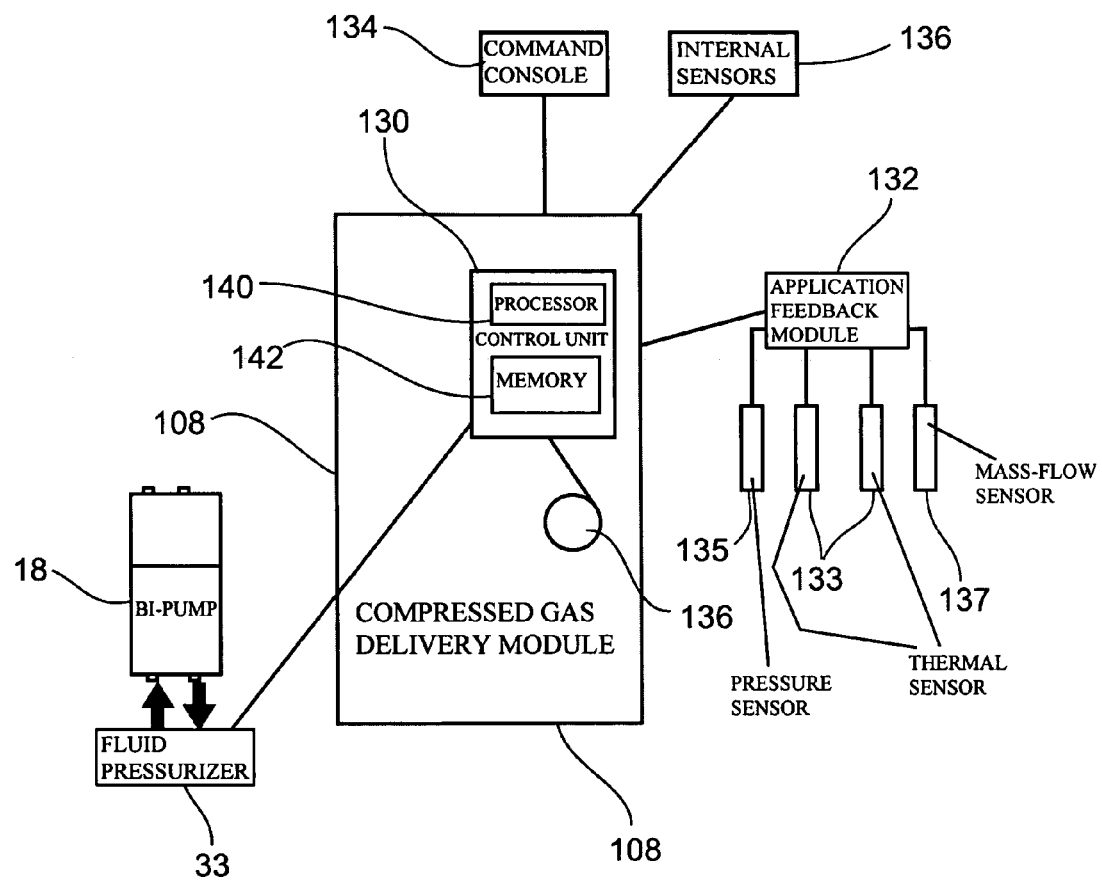
FIG. 6 is a compressed gas delivery module, according to the present invention.

In a preferred embodiment presented in FIG. 6, compressed gas delivery module 108 further includes control elements for managing gas compression. A control unit 130 receives information from application feedback element 132. In the case a preferred embodiment in which compressed gas utilizing application 42 is a cryosurgery system 110, application feedback element 132 is plurality of thermal sensors 133, reporting on temperatures within various parts of cryosurgery application 110, such as within cryoprobes 112. Other optional sensors included in feedback element 132 are a pressure sensor 135 and a mass flow sensor 137. Control unit 130 also receives information from internal sensors 136, which typically include pressure sensors and other, e.g., temperature sensors.

Control unit 130 also receives information and commands from an optional command console 134 for receiving commands from a user, and from optional remote command module 136, which is a data source such as an infrared remote control unit or other telecommunications device.

Control unit 130 optionally includes a processor 140 and memory 142, used to coordinate and control various parts of the system. In a preferred embodiment, processor 140 is operable to control gas compression and gas flow according to a set of programmed instructions stored in memory 142. Output from control unit 130 goes to control elements of gas delivery control system 108, such as valves controlling flow of gas. In a preferred embodiment utilizing bi-pump 18, output from control until 130 also goes to control elements of fluid pressurizer 33 of bi-pump 18, for controlling the output pressure of fluid pressurer 33 and thereby controlling a compressed gas pressure of a compressed gas supplied by bi-pump 18 through compressed gas manifold 106 to compressed gas delivery module 108.

Figure 7:
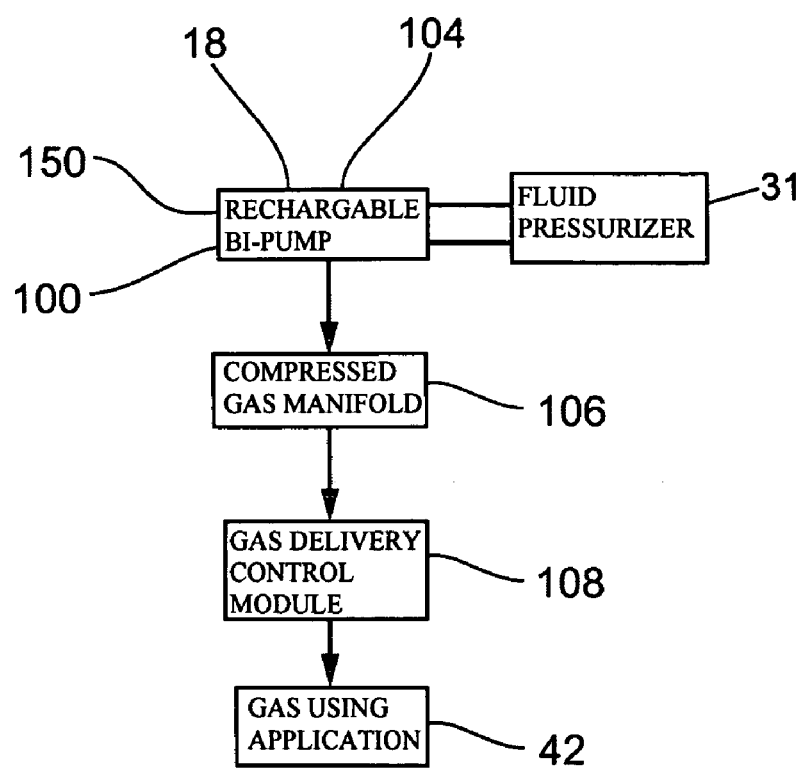
FIG. 7 is a compressed gas utilization system incorporating a rechargeable gas compression apparatus, according to the present invention.

Yet another embodiment of a compressed gas utilization system according to the present invention is presented by FIG. 7. In this preferred embodiment, gas source 100 and bi-pump 18 are combined into a single element, a rechargeable bi-pump 150. In a first phase of operation, rechargeable bi-pump 150 is disconnected from fluid pressurizer 33 and from compressed gas manifold 106, and is typically transported to a source of medium pressure gas, such as an industrial gas supply source, where rechargeable bi-pump 150 is recharged with medium pressure gas in much the same way that classical gas cylinders are recharged with compressed gas.

In a second phase of operation, recharged rechargeable bi-pump 150 is re-connected to fluid pressurizer 33 and to gas output manifold 106. Fluid pressurizer 33 then applies pressure to pressurizing fluid 32, as described hereinabove, further pressurizing gas in gas portion 24 of rechargeable bi-pump 150, raising the pressure of a gas contained therein up to a pressure required by compressed gas utilizing application 42. Compressed gas is then supplied through gas output manifold 106 and gas delivery control module 108 to compressed gas utilizing application 42.

The embodiment of FIG. 7 has several advantages over prior art, in particular the advantage that rechargeable bi-pump 150 can be charged to medium pressure at an industrial gas supply source, yet can supply high pressure gas to compressed gas utilizing application 42. The embodiment presents the further advantage that substantially all the gas supplied in a charged rechargeable bi-pump 150 can be delivered at high pressure to compressed gas utilizing application 42, in distinct contrast to prior art systems in which a substantial portion of the gas supplied in a traditional gas supply cylinder or similar container cannot be so used. Further, the embodiment of FIG. 7 presents the additional advantage of simplicity.

Yet, the embodiment of FIG. 7 does present a disadvantage, in that rechargeable bi-pump 150 must contain sufficient gas to effect the entire operation of compressed gas utilizing application 42, or else operation of compressed gas utilizing application 42 must be interrupted while an emptied rechargeable bi-pump 150 is replaced by a recharged rechargeable bi-pump 150.

Figure 8:
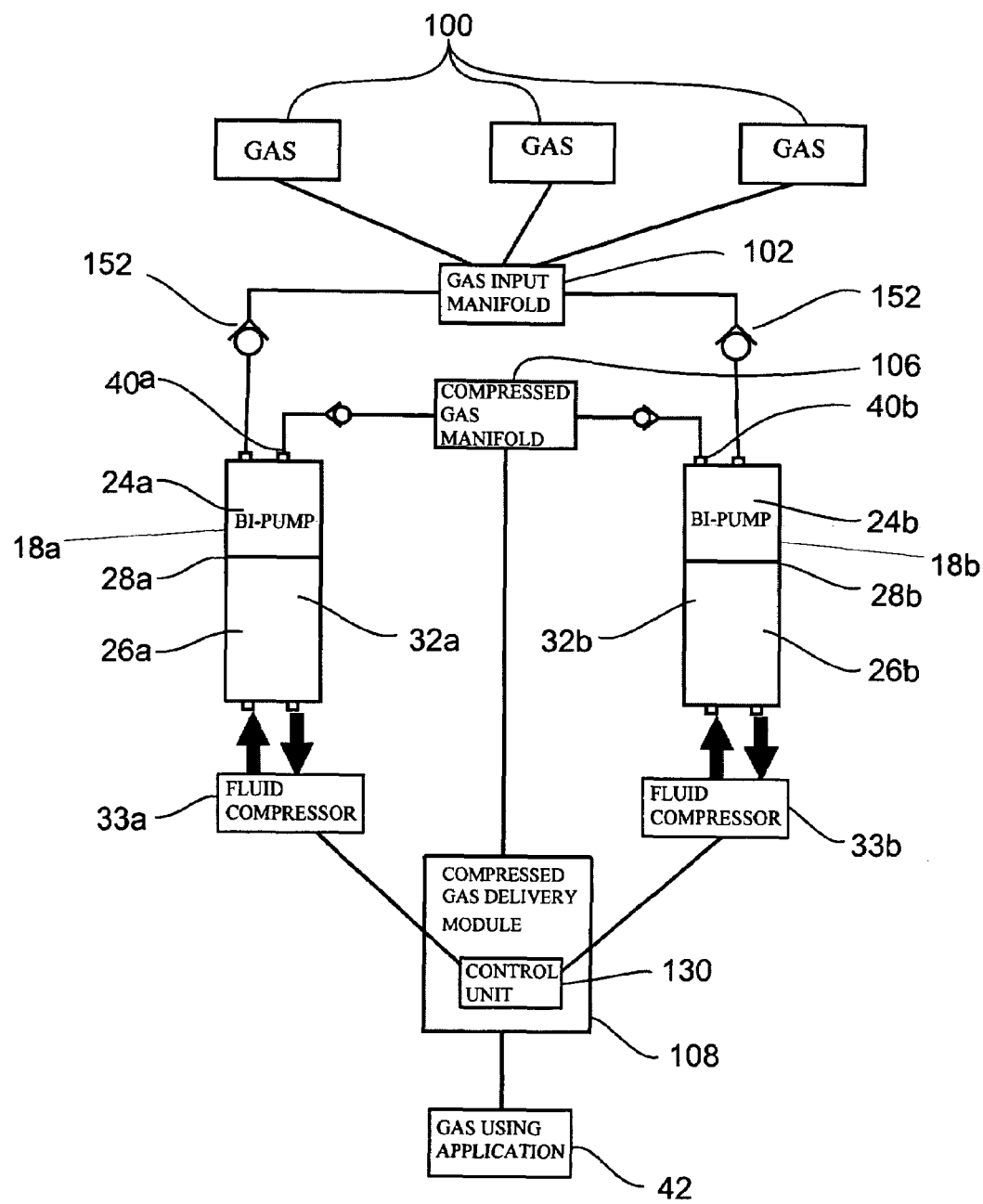
FIG. 8 is a compressed gas utilization system utilizing a plurality of gas compression apparati.

FIG. 8 presents an alternative construction of another preferred embodiment of the present invention, one which allows for continuous operation of compressed gas utilizing application 42. In this embodiment gas input manifold 102 supplies gas to a plurality of bi-pumps 18, represented in FIG. 8 by bi-pumps 18*a* and 18*b*. Gas input manifold 102 supplies gas to bi-pumps 18*a* and 18*b* through one-way filters 152 which allow gas to flow from gas input manifold 102 towards bi-pumps 18*a* and 18*b*, but do not allow gas to flow from bi-pumps 18 towards gas input manifold 102. Control unit 130 of gas delivery module 108 controls fluid pressurizers 33*a* and 33*b* in such a manner that when bi-pump 18*a* is in its first phase of operation bi-pump 18*b* is in its second phase of operation, and vice versa.

Thus, during a first period, bi-pump 18*a* is in a first phase of operation, during which pressurizing fluid 32*a* in fluid portion 26*a* is not under pressure, and is indeed allowed to drain from bi-pump 18*a* into fluid pressurizer 33*a*. Gas pressure from gas input manifold 102, under pressure from at least one gas source 100, exerts pressure on moving partition 18*a*, causing gas portion 24*a* to expand and allowing gas portion 24*a* to fill with gas from gas input manifold 102. Movement of moveable element 28*a* also causes or assists pressurizing fluid 32*a* to drain from fluid portion 26*a*. Also during this first period, bi-pump 18*b* is in its second phase of operation, during which pressurizing fluid 32*b* is supplied by fluid pressurizer 33*b* under pressure, compressing gas in gas portion 24*b*, which is then supplied through gas output coupling 40*b* to output gas manifold 106 and thence to compressed gas delivery module 108 and thence to compressed gas utilizing application 42.

During a second period, the roles of bi-pump 18*a* and of bi-pump 18*b* are reversed. Bi-pump 18*a* enters into its second phase of operation, fluid pressurizer 33*a* pressurizes pressurizing fluid 32*a*, thereby compressing a gas in gas portion 24*a* of bi-pump 18*a*. Compressed gas from gas portion 24*a* is supplied through gas output coupling 40*a* to gas output manifold 106 and then to compressed gas delivery module 108 and thereafter to compressed gas utilizing application 42. Also during this second period, bi-pump 18*b*, which was partially or completely emptied of gas during the first period, is refilled: pressure from fluid pressurizer 33*b* is relaxed, pressurizing fluid 32*b* is allowed to drain from fluid portion 26*b* of bi-pump 18*b*, and the relaxed pressure in fluid portion 24*b* allows gas pressure from input gas manifold 102 to move moveable element 28*b*, expanding gas portion 24*b* and filling gas portion 24*b* with gas, while assisting in draining pressurizing fluid 32*b* from fluid portion 26*b*.

Alternating first periods and second periods enables the system of FIG. 8 to provide a continuous supply of pressurized gas to compressed gas utilizing application 42. In the first period bi-pump 18*a* fills with gas while bi-pump 18*b* supplies compressed gas for compressed gas utilizing application 42, then in the second period bi-pump 18*b* fills with gas while bi-pump 18*a* supplies compressed gas for compressed gas utilizing application 42. The process then repeats, and can be repeated indefinitely, so long as a gas source 100 is available to supply gas to gas input manifold 102. An external or internal gas cylinder or other gas supply container can supply gas as many as several times to fill a bi-pump 18, the gas being supplied each time at somewhat lower pressure as the supply cylinder gradually empties. Moreover multiple gas sources 100, multiple gas supply cylinders for example, may be connected to gas input manifold 102, hence it is possible to replace an empty gas source 100 such as an empty gas supply cylinder with a full gas source 100 such as a charged gas supply cylinder, without interrupting a flow of gas from at least one gas supply source 100 to gas input manifold 102. Thus, the embodiment of FIG. 8 enables continuous gas compression and continuous supply of compressed gas to compressed gas utilizing application 42.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for cryosurgery, involving in situ compression of gas, comprising:
   (a) using a first in situ gas compressor which comprises a fixed-volume container having a hollow and a moveable element subdividing said hollow into a first variable-volume portion and a second variable-volume portion, by introducing a hydraulic and/or pneumatic fluid under pressure into said second variable-volume portion, thereby causing an increase in a volume of said second variable-volume portion by moving said moveable element, thereby decreasing volume of said first variable-volume portion, thereby compressing a gas contained therein, thereby transforming said gas contained therein into a first compressed gas at a first gas pressure;
   (b) transferring said first compressed gas at said first gas pressure from said first gas compressor to a cryoablation apparatus utilizing said first compressed gas at said first gas pressure;
   (c) using said cryoablation apparatus to perform cryoablation, thereby creating a depressurized gas at a second gas pressure;
   (d) transporting said depressurized gas at said second gas pressure to said first gas compressor, for recompression and reuse; and
   (e) recompressing and reusing said depressurized gas.

2. The method of claim 1, wherein said cryoablation apparatus comprises a Joule-Thomson heat exchanger for cooling a portion of said cryoablation apparatus.

3. The method of claim 2, wherein said transporting comprises transporting using a mechanism for transporting said gas depressurized by use in said Joule-Thomson heat exchanger from said cryoablation apparatus to said gas compressor.

4. The method of claim 3, wherein said mechanism for transporting a gas includes a second gas compressor.

5. The method of claim 3, wherein said mechanism for transporting a gas includes a gas reservoir.

6. The method of claim 3, wherein said first variable-volume portion of said first gas compression apparatus is coupled during a first phase of operation to said mechanism for transporting a gas depressurized by use in said Joule-Thomson heat exchanger from said cryoablation apparatus to said first gas compressor, and said first variable-volume portion of said first gas compression apparatus is coupled during a second phase of operation to a mechanism for transporting a compressed gas from said first variable-volume portion of said first gas compression apparatus to said cryoablation apparatus.

7. The method of claim 1, wherein said first gas compressor comprises a first refillable unit operable to be filled through a first input portal with a first pressurized gas at a first pressure, and further operable to supply said gas to said cryoablation apparatus at a second pressure when a fluid pressurizer supplies a pressurizing fluid pressurized to said second pressure at a second input portal of said first refillable unit.

8. The method of claim 7, wherein said first refillable unit is portable.

9. The method of claim 7, wherein said first gas compressor comprises a second refillable unit.

10. The method of claim 9, wherein said first refillable unit is operable to be refilled with said gas at said first pressure while said second refillable unit provides gas to said cryoablation apparatus at said second pressure.

11. The method of claim 9, wherein said second refillable unit is operable to be refilled with said gas at said first pressure while said first refillable unit provides gas to said cryoablation apparatus at said second pressure.

12. The method of claim 1, wherein said moveable element is a piston.

13. The method of claim 1, wherein said moveable element is a bladder.

14. The method of claim 1, wherein said moveable element is a diaphragm.

* * * * *